United States Patent
Magnan et al.

(10) Patent No.: US 6,203,571 B1
(45) Date of Patent: Mar. 20, 2001

(54) MIDDLE EAR PROSTHESIS

(75) Inventors: Jacques Magnan, Roquevaire; Loic Giquel, Dinard; Bernard Prandi, Seythenex, all of (FR)

(73) Assignee: Nogitek, Saint Gregoire (FR)

( * ) Notice: Subject to any disclaimer, the term of this patent is extended or adjusted under 35 U.S.C. 154(b) by 0 days.

(21) Appl. No.: 09/167,661

(22) Filed: Oct. 7, 1998
(Under 37 CFR 1.47)

(30) Foreign Application Priority Data

Oct. 10, 1997 (FR) .................................................. 97 12995

(51) Int. Cl.[7] ........................................................ A61F 2/18
(52) U.S. Cl. ................................................................ 623/10
(58) Field of Search .................................................. 623/10

(56) References Cited

U.S. PATENT DOCUMENTS

| | | |
|---|---|---|
| 4,728,327 * | 3/1988 | Gersdorff ........................... 623/10 |
| 4,957,507 | 9/1990 | Lenkauskas . |

FOREIGN PATENT DOCUMENTS

| | | |
|---|---|---|
| 379740 | 8/1990 | (EP) . |
| 2691354 | 11/1993 | (FR) . |
| 0993934 * | 2/1983 | (SU) ..................................... 623/10 |
| 1634272 | 3/1991 | (SU) . |
| 9218066 | 10/1992 | (WO) . |

* cited by examiner

Primary Examiner—David J. Isabella
(74) Attorney, Agent, or Firm—Dowell & Dowell, P.C.

(57) ABSTRACT

A middle prosthesis including an element comprising an arched section defining first and second branches which are spaced from one another and are movable relative to one another by the elasticity of the element and wherein the element is formed of a superelastic metal alloy.

11 Claims, 4 Drawing Sheets

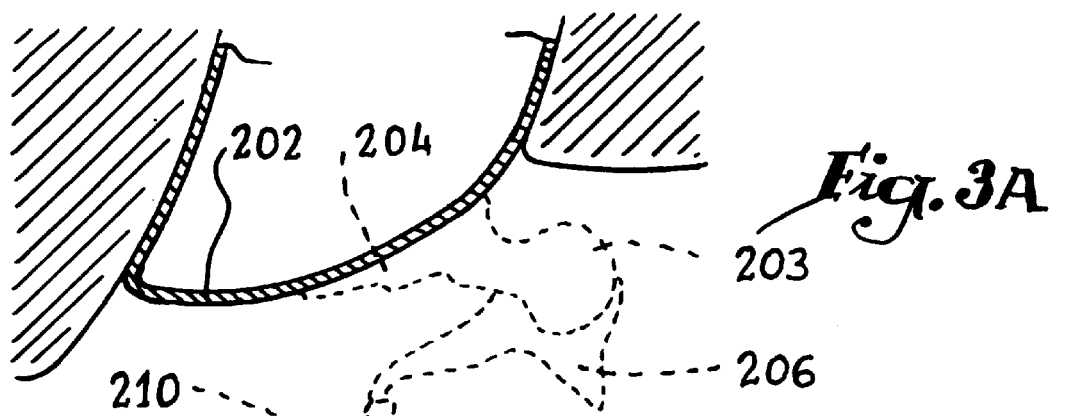
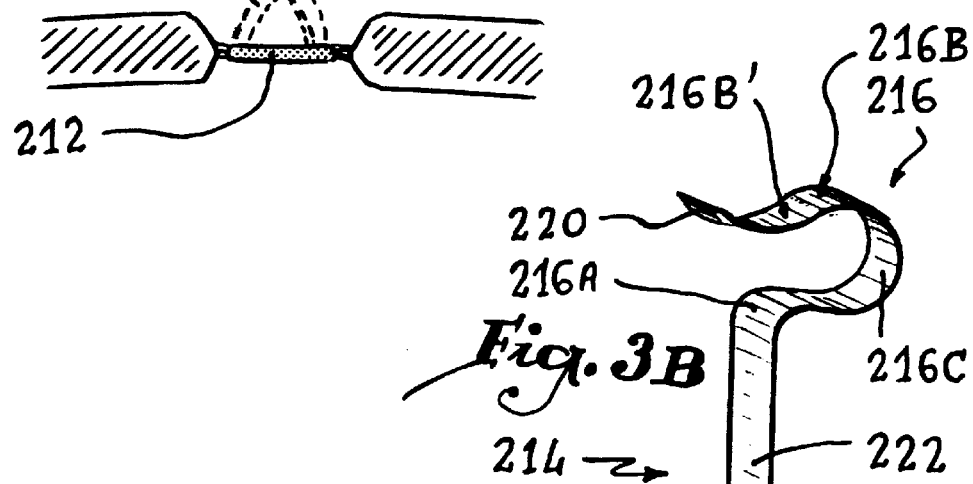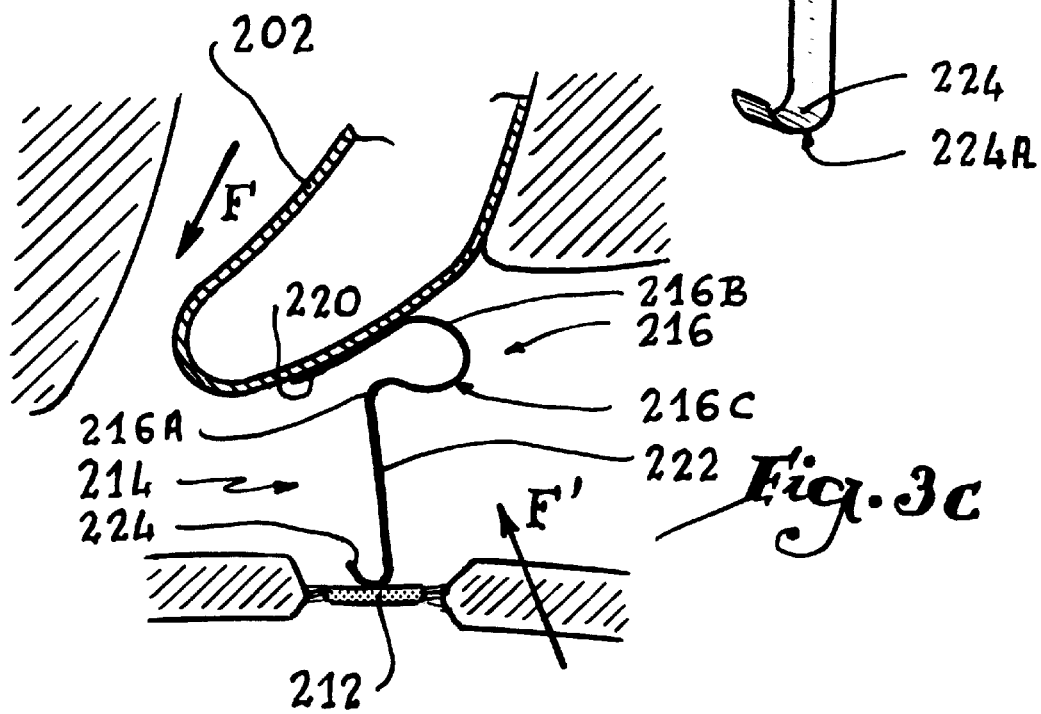

MIDDLE EAR PROSTHESIS

BACKGROUND OF THE INVENTION

1. Field of the Invention

The present invention relates to an ossicular prosthesis of the middle ear, of such a type as to replace at least partly the ossicular chain and to link a first organ or element, particularly the foot plate or the stirrup or stapes, with a second organ or element, particularly the hammer or malleus or the eardrum, which prosthesis can self-adjust by elasticity.

2. Brief Discussion of the Related Art

The middle ear has the task to convey the sound vibrations reaching the eardrum from an aerial environment to a watery environment, namely the inner ear, which constitutes a receiver element of perception of a sound wave.

The conduction of the latter is effected by an anatomic element, called the middle ear conductive system, constituted by a tympanic membrane adjoining an ossicular chain formed, from the outside to the inside, by the malleus, the anvil or incus and the stapes. The tympanic membrane adjoins this chain by the handle of the malleus. The stapes rests on a plate which on its internal base enters into contact with the watery environment, also called labyrinthine environment, of the inner ear.

The function of the ossicles of ossicular chain is to establish the contact between the eardrum and this labyrinthine environment, which constitutes the columellar effect. The ossicular eardrum system is suspended in the aerial cavity of the middle ear. Thus, there is no direct contact of this system with the osseous walls in order to convey acoustic energy originating from the tympanic membrane, namely the external ear, towards the inner ear.

The fixation point of the ossicular eardrum system are two annular ligaments situated at its extremities, namely that of the tympanic membrane and that of the foot plate.

The object of the present invention is to correct the conductive hearing loss, namely resulting from disorders on the ossicular chain after different pathologies.

The ossicular prosthesis for the middle ear have the purpose of replacing, at least partially, this ossicular chain, be it only the incus, the stapes and the incus, or also the stapes, the incus and the malleus.

Until now the available prosthesis are made out of various materials, such as a ceramic material, and consisting of a rod or shaft resting on the head of the stapes or on the foot plate, topped by a platform that makes contact with the handle of the malleus or on the eardrum. Because of the nature of the constructive material, these prostheses present an essentially rigid construction.

This solution presents a number of disadvantages. Thus, first of all, it is necessary that the surgeon has at his disposition a large number of prosthesis of different sizes and shapes, in order to be able to choose among them the most appropriate one for the implantation to be effected.

Furthermore, it is necessary to modify the size of these types of prosthesis, either by cutting them or by milling them so as to adapt their sizes to those of the "defects," namely of the elements missing from the ossicular chain. This brings about a modification of the condition of the surface of the prosthesis, which contributes to weaken it, to locally modify its interface, and constituting an attraction for an inflammatory reaction.

Lastly, in view of the fact that these prostheses are rigid and have dimensions that cannot be modified, their anchoring point on the elements which they are supposed to link consists of a simple contact, so that the prosthesis is placed only under a passive tension between these elements. This does not allow the reconstitution of a perfectly stable unit, even after an accurate placing of the prosthesis, which explains the many displacements that were observed after an operation. Thus, only about 75% of the partial prostheses, and 50% of the total ones, have shown to have a sufficient mechanical resistance.

In order to remedy these problems of stability, other middle ear prosthesis were suggested, in particular in WO-A-92/18066. This document describes a prosthesis constituted by two independent elements maintained in contact, of which one moves with respect to the other by means of a mechanical spring-system. Such adaptation provides a possibility of deformation of the prosthesis while being its installed. However, the mechanical stresses exercised by these prosthesis on the elements they link are not constant due to the fact of the frictional forces taking place between the two constituent elements of the prosthesis. This leads to a great risk of traumatism at the surfaces of the elements in contact with this prosthesis. Moreover, the latter presents a relatively complex mechanical structure which leads to a high cost, and wherein the functioning can be altered by the presence of tissues at the spring.

SUMMARY OF THE INVENTION

The present invention has the purpose of overcoming the disadvantages of the above described type of prosthesis.

For this purpose, it has as object a middle-ear prosthesis of above-mentioned type, characterized by the fact that it is constituted by an elongated element that comprises an essentially C-shaped or arched section, intended to enter into contact with at least one of the elements with an external surface of at least one of its branches, which branches are suitable to come closer to each other or to move apart by elasticity.

The end of the elongated element designates an element formed, at least partly, by a thin strip.

The prosthesis in accordance with the invention allows to achieve the above-mentioned objectives. Thus, it presents an extremely simple mechanical structure, since it is formed by one only element which, while being installed, does not have to be cut nor milled, which allows the reduction of the risks of an inflammatory reaction and consequently the phenomena of ossicular lysis.

Furthermore, in view of the fact that the branches of the arched section are such that they can come closer to each other or move apart by elasticity, the dimensions of the prosthesis and those that separate the elements it must link are perfectly adapted to each other. The elastic nature of this arched section allows it to self-adjust, not only with respect to the various sizes according to the patients, but also according to the vibrations exercised by the postoperative fibrosis at the eardrum surface. Thus, this ensures a very satisfactory stability of the prosthesis in accordance with the invention.

Furthermore, this arched section presents sufficient flexibility, so that it can be installed without an excessive tension at the time when it is placed and that, after its installation, it can exert an almost constant, permanent tension at its respective anchoring points.

According to a first embodiment of the invention, the arched section is intended to enter into contact with the handle of the malleus and the eardrum by the external surface of its two branches. In this embodiment, the prosthesis in accordance with the invention, constitutes an incus prosthesis allowing to link the malleus and the stapes.

According to an additional characteristic of the invention, a notch intended to house the end-foot of the stapes is provided in the second branch of the arched section. This guarantees a satisfactory, long-term anchoring of the entire prosthesis with the stapes.

According to a second embodiment of the present invention, the arched section is intended to enter into contact with one of the elements by the external surface of a first branch and, at the second branch, it is extended by an essentially rectilinear section. This essentially rectilinear section makes it possible that the prosthesis in accordance with the invention rests against the footplate of the stapes, so that it can constitute either a total incus and stapes prosthesis or also a malleus, incus and stapes prosthesis. This rectilinear section assumes further the function of conveying the sound vibrations to the foot plate of the stapes. In the case of a partial prosthesis, the rectilinear section is essentially arranged in the extension of the second branch, while in the case of a total prosthesis the rectilinear section is almost perpendicular to this second branch.

According to an additional characteristic of the invention, the rectilinear shaft or section is extended by a curved section, which extension is at its end opposite of the arched section. This curved section rests against the foot plate of the stapes and ensures a good stability of the prosthesis with respect to the latter.

According to an additional characteristic of the invention, the arched section is extended, at its first branch, by a curved section, the concavity of which is oriented opposite to the rectilinear section. This curved section ensures a satisfactory holding of the prosthesis on the first element it is intended to link, namely, the eardrum or the malleus.

In accordance with an advantageous characteristic of the invention, the prosthesis is made out of a superelastic metal alloy at body temperature. By superelastic alloy must be understood any alloy of which the elasticity range is greater than that of the standard metals, and for which the stress exerted on the elasticity bearing is practically constant.

According to a preferred characteristic of the invention, the superelastic alloy is a forming memorious alloy.

A forming memorious alloy presents on either side of a transition temperature a heat-resistant, austenitic crystalline structure and a cold-resistant, martensitic structure. Moreover, when a part made out of a forming memorious alloy is subjected to a stress in its austenitic structure, its structure becomes at least partly martensitic which leads to a very high elastic deformation that could reach up to 8%.

The use of superelastic metal alloys and, specifically, forming memorious alloys is particularly advantageous. In fact, the arched section itself absorbs all the pressures during the installation by adjusting its dimensions. Moreover, this arched section adapts its geometry according to the size of the "defect," namely of the elements of the ossicular chain it is intended to replace. Because of its superelastic nature, this arched section exerts on the eardrum a very slight and essentially constant force which is particularly advantageous with respect to the physiological integrity of the eardrum and the foot plate.

Once the prosthesis is in place, its rectilinear section has an austenitic structure which allows it to possess the necessary rigidity properties to ensure a satisfactory conveyance of the vibrations while, according to the extent of the deformation, its arched section can have a structure at least partly martensitic.

According to an advantageous characteristic of the invention, the forming memorious alloy has an end of occurrence austenitic temperature ($A_f$) without mechanical stress, that is lower than 30° C. and, preferably, lower than 20° C.

According to an additional characteristic of the invention, the forming memorious alloy is constituted by titanium and nickel, and contains 55.7%±4% of nickel.

BRIEF DESCRIPTION OF THE DRAWINGS

The invention is described below, making reference to the accompanying illustrations, given only by way of example, and in which:

FIG. 3A shows, in dotted lines, a completely missing ossicular chain;

FIG. 3B shows a third prosthesis in accordance with the invention, and

FIG. 3C shows the prosthesis illustrated in FIG. 3B and replacing the ossicular chain of FIG. 3A.

DESCRIPTION OF THE PREFERRED EMBODIMENTS

Figure 1A:
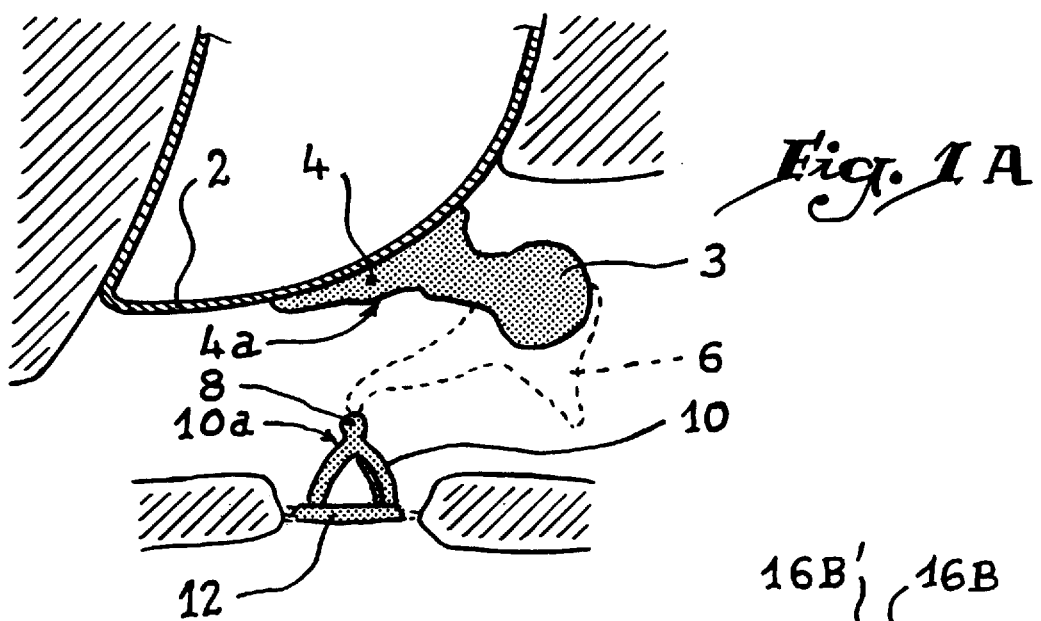
FIG. 1A shows an incomplete ossicular chain in which the incus is missing.

FIG. 1A illustrates the middle ear of a patient. It includes, from the outside to the inside, an eardrum 2 adjoining the malleus 3 at its handle 4. The head of the malleus presents, in the rear, an articular surface that is intended to unite with the incus 6 whose lenticular apophysis is articulated with the head 8 of the stapes 10. The internal base of the foot plate 12 of the stapes is oriented toward the solum of the vestibule of the not represented inner ear.

The ossicular chain, constituted by the malleus, the incus and the stapes, is incomplete in as much as the incus 6 is missing and, because of this, it is represented by broken lines.

In what follows, and for the sake of clarity, the head of the patient is in the operating position, that is to say, decubitus dorsal, with the head turned to the opposite side of the illustrated ear, herein the left ear.

Figure 1B:
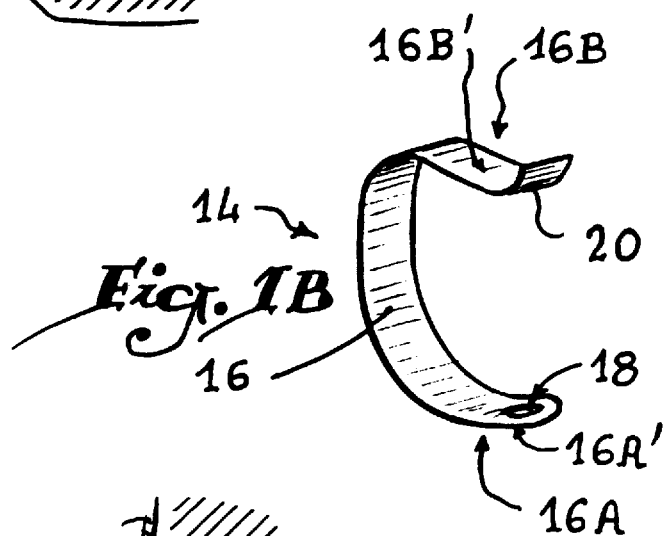
FIG. 1B shows a first prosthesis in accordance with the invention.

FIG. 1B shows a prosthesis designated in its entirety by the reference number 14 and intended to replace the incus 6 in the ossicular chain of FIG. 1A.

This prosthesis is made out of a forming memorious alloy, constituted by 55.75% of nickel and 44.25% of titanium, whose structure is superelastic with respect to the body temperature.

This prosthesis 14 comprises an essentially arched section 16, whose lower branch 16A is provided with a transversing notch or orifice 18 and the upper branch 16B is extended by a curved section 20, the concavity of which is oriented opposite to the lower branch 16A intended to make contact with the handle 4 of the malleus.

Figure 1C:
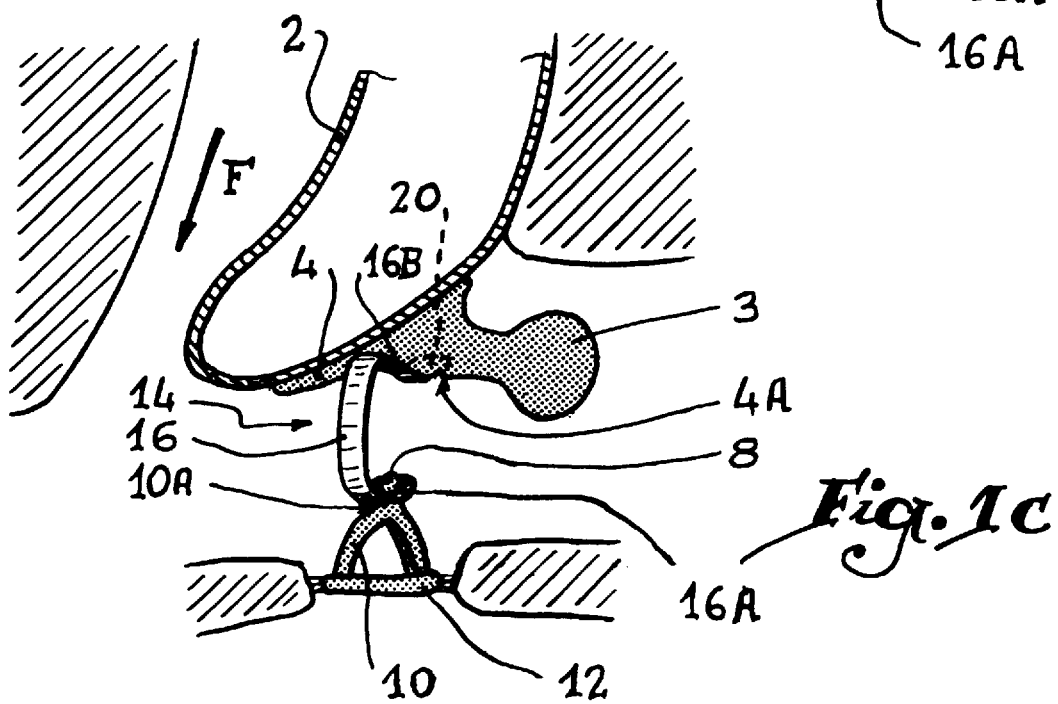
FIG. 1C shows the prosthesis illustrated in FIG. 1B, inserted in the ossicular chain of FIG. 1A.

The distance separating the two branches 16A, 16B is slightly greater than the one separating the head 8 of the stapes with respect to the lower surface o the handle 4 of the malleus. In this manner, as shown in FIG. 1C, the external surface 16B' of the upper branch 16B rests, once the prosthesis is installed, against the lower surface 4A of the handle 4. Further, the external surface 16A' of the lower branch 16A enters into contact with the upper surface 10A of the stapes 10, the notch 18 of this branch 16A fitting over the head 8 of the stapes.

The placing of the prosthesis in accordance with the invention is effected in a known manner, be it by way of the external auditory canal or by endaural approach, according to the arrow F, or by way of the posterior tympanotomy according to arrow F'. For this, the surgeon places the orifice 18 over the head 8 of the stapes. The superelastic nature of the used alloy makes it possible to bend the prosthesis so as to bring its branches 16A and 16B closer together, which allows to easily slide the upper branch 16B under the handle 4 of the malleus.

Figure 1D:
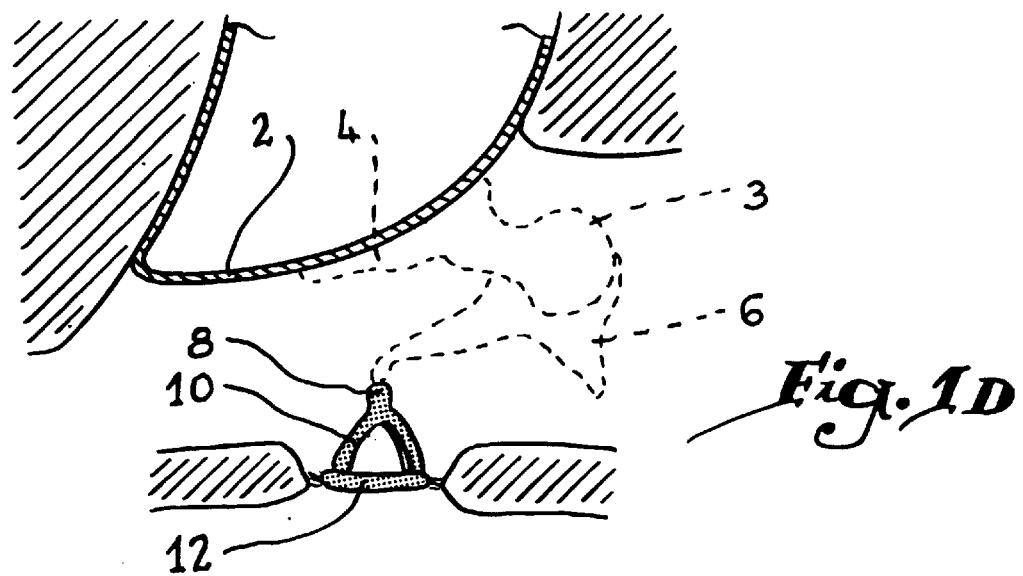
FIG. 1D shows an incomplete ossicular chain in which the incus and the malleus are missing.
Figure 1E:
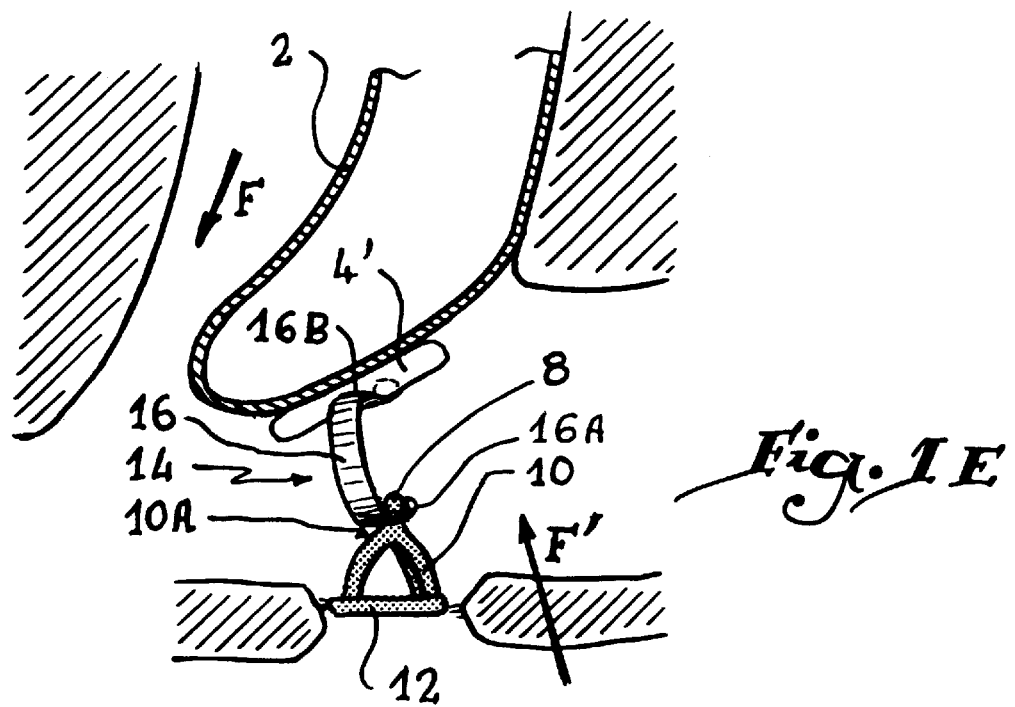
FIG. 1E shows the prosthesis illustrated in FIG. 1B, inserted in the ossicular chain of FIG. 1D.

The prosthesis 14 in accordance with the invention can also be used in cases when the malleus is missing. FIG. 1D shows the incomplete ossicular chain in as much as the incus and the malleus are missing, because of which they are represented by broken lines.

The placing of the prosthesis 14 in accordance with the invention on the head 8 of the stapes is effectuated in the same manner as described above. The malleus 4 is replaced with a cartilaginous fragment 4', intended to enter into contact with the upper branch 16B of the prosthesis 14.

Further, the geometry of the curved section 20 guarantees a perfect complementarity of the shapes between the handle 4 or the cartilaginous fragment 4' and the prosthesis. The superelastic nature of the latter makes it possible that it can be adapted not only according to the sizes of the missing elements of the different patients but also according to the stresses exerted by the stapes and the malleus.

Figure 2A:
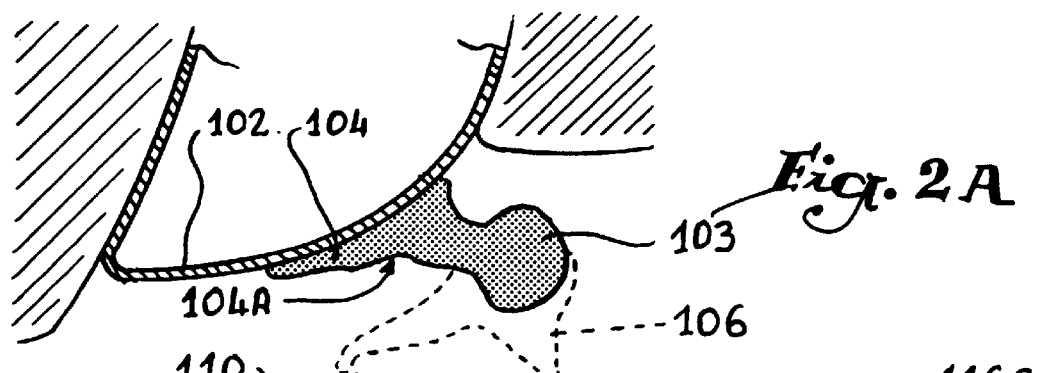
FIG. 2A shows an incomplete ossicular chain in which the stapes and the incus are missing.

The ossicular chain illustrated in FIG. 2A differs from the one illustrated in FIG. 1A in that not only the incus 106 but also the arch of the stapes 110 are missing, because of which they are represented by broken lines. The prosthesis 114, illustrated in FIG. 2B and intended to replace these two elements, comprises an essentially arched section 116, of which a first branch 116B, or a distal branch is extended by a curved section 120, essentially analogous to the section 20, illustrated in FIGS. 1B and 1C. The second branch 116A of this arched section 116, or proximal branch, extends by means of an essentially rectilinear section 122 oriented according to the extension of this lower branch 116A. This rectilinear section 122 ends in a curved section 124, projecting essentially in a right angle starting at the rectilinear section 122 in the direction of the segment 116C of the arched section.

The distance that separates the external surface 116B' of the distal branch 116B from the lower surface 124A of the curved section 124 is slightly greater than the distance separating the foot plate 112 from the lower surface 104A of the handle 104 of the malleus 103.

The installation of the prosthesis 114 is effected by placing the lower surface 124A of the curved section 124 on the foot plate 112, then bringing closer the distal branch 116B of the arched section 116 in direction of the proximal branch 116A, thanks to the nature of the superelastic material used.

Then it is easy to insert this proximal branch 116A under the handle 104 of the malleus 103. This placing of the prosthesis is simple and does not entail a damaging of the ossicular elements intended to enter into contact with the prosthesis.

In view of the fact that the arched section 116 is subjected to stresses exerted by the malleus and the foot plate of the stapes, it presents a structure at least partly martensitic. Its branches 116A, 116B can thus be adapted according to the size of the ossicular chains of the different patients and to the stresses exerted on the malleus and the foot plate 112 of the stapes at the time of the tenting or of the postoperative fibrosis, which imparts an excellent stability to the prosthesis, The rectilinear section 112 itself presents an austenitic structure which gives it a rigidity that allows it to transmit the sound vibrations from the eardrum 102 up to the labyrinthine environment of the inner ear.

The middle ear, illustrated in FIG. 3A, is without the entire ossicular chain, since the malleus 203, the incus 206 and the entire structure of the stapes 210 are missing, because of which they are illustrated by broken lines.

The prosthesis 214 is intended to replace this entire ossicular chain. It comprises an essentially arched section 216, the upper branch 216B of which ends in a curved section 220, the concavity of which is oriented opposite to the lower branch 216A of the arched section. This lower branch 216A is extended by a rectilinear section 222 which, essentially in a right angle, joins the arched section. This rectilinear section 222 ends in a curved section 224 effecting an uncoupling in an essentially right angle, projecting in an opposite direction to the center 216C of the arched section.

The distance separating the external surface 216B' from the upper branch 216B and the lower surface 224A of the curved section 224 is slightly greater than the distance separating the eardrum 202 from the foot plate 212.

Figure 2B:
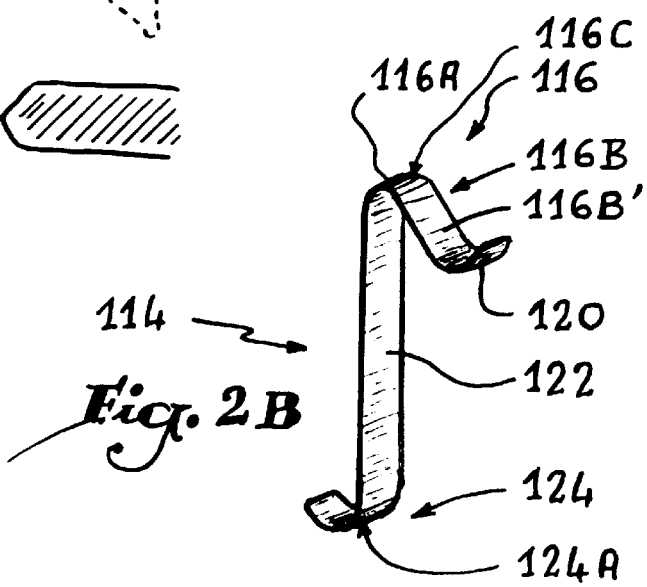
FIG. 2B shows, in perspective, a second prosthesis in accordance with the invention.
Figure 2C:
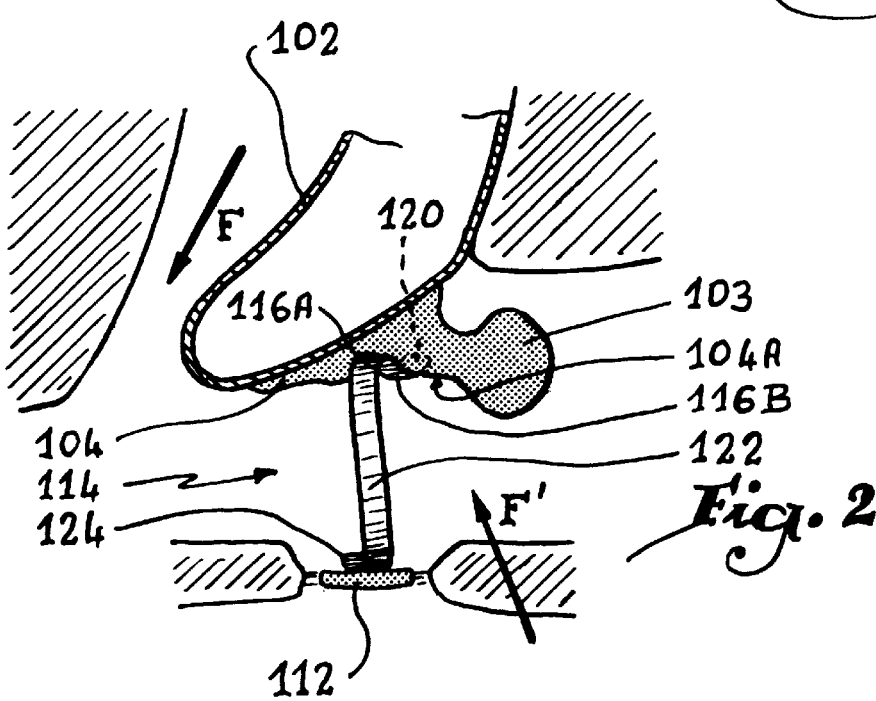
FIG. 2C shows the prosthesis illustrated in FIG. 2B, inserted in the ossicular chain of FIG. 2A.

The placing of the prosthesis 214 is carried out in a manner analogous to the one described in the FIGS. 2A to 2C, either according to the arrow F by way of the external auditory canal or to the arrow F' by way of the posterior tympanotomy. The surgeon brings the branches 216A, 216B closer to each other by taking advantage of the superelastic nature of the constituent alloy of the prosthesis, which allows the latter to be inserted without damaging neither the foot plate nor the eardrum.

Once the prosthesis is installed, it is supported against the eardrum 202, simultaneously by its upper branch 216B and its curved section 220, of which the shape ensures a perfect complementarity of the shapes with the eardrum. The prosthesis rests with its lower surface 224A of its curved section 224 on the foot plate 212 of the stapes.

The arched section 216 is subjected to the stresses exerted by the eardrum and the foot plate of the stapes and has an austenitic structure, or at least partly martensitic, depending on the intensity of these stresses. The dimensions of this arched section 216 are also susceptible to be adapted not only according to the size of the various ossicular defects of the patients but also to the stresses simultaneously exerted on this section by the eardrum and the foot plate of the stapes. It must be noted that, due to its superelastic nature, the reaction forces exerted on the eardrum and the foot plate of the stapes by the arched section and the curved section, respectively, are very slight and essentially constant. This is particularly advantageous for the maintaining of the physiological integrity of the eardrum and the foot plate, and to ensure a satisfactory stability of the thus reconstructed ossicular chain.

Further, the rectilinear section 222, that presents an austenitic structure, thanks to its rigidity properties can also assume in a satisfactory manner the conveyance of the sound vibrations.

What we claim is:

1. An ossicular prosthesis for a middle ear which is adapted to replace at least one component of an ossicular chain to thereby physically link a foot plate of a stapes to an eardrum, wherein the prosthesis includes an element formed of a superelastic metal alloy at body temperature having a generally c-shaped portion defined by first and second branches which are spaced from one another and which are movable relative to one another by elasticity of said generally c-shaped portion, and at least one of said first and second branches having an external surface adapted to engage one of a component of the ossicular chain, the foot plate of the stapes and the eardrum.

2. The ossicular prosthesis of claim 1 wherein each of said first and second branches includes an end portion, and each of said end portions including an external surface adapted to engage one of a component of the ossicular chain, the foot plate of the stapes and the eardrum.

3. The ossicular prosthesis of claim 2 in which said end portion of said second branch includes an orifice therein adapted to receive an end-foot of the stapes therein.

4. The ossicular prosthesis of claim 3 in which said external surface of said end portion of said first branch is concavely curved in a direction away from said second branch.

5. The ossicular prosthesis of claim 1 wherein said second branch includes a rectilinear section extending from said first branch.

6. The ossicular prosthesis of claim 5 in which said rectilinear section extends to an outer end portion of said second branch which is reversely curved with respect to said generally c-shaped portion.

7. The ossicular prosthesis of claim 1 in which said first branch includes an external surface concavely curved in a direction away from said second branch.

8. The ossicular prosthesis of claim 1 wherein said superelastic alloy is a forming memorious alloy.

9. The ossicular prosthesis of claim 8 wherein said alloy has an end of an occurrence austenitic temperature without mechanical stress that is lower than approximately 30° C.

10. The ossicular prosthesis of claim 9 in which said alloy has an end of an occurrence austenitic temperature without mechanical stress of lower than approximately 20° C.

11. The prosthesis of claim 8 wherein said alloy is a titanium and nickel alloy containing 55.7%±4% of nickel.

* * * * *